(12) United States Patent
Siegel et al.

(10) Patent No.: US 8,568,512 B2
(45) Date of Patent: Oct. 29, 2013

(54) METHOD AND SYSTEM FOR METHANE SEPARATION AND PURIFICATION FROM A BIOGAS

(75) Inventors: Stanley M. Siegel, West Newton, PA (US); Dennis C. Siegel, Alverton, PA (US)

(73) Assignee: A.R.C. Technologies Corporation, Yukon, PA (US)

( * ) Notice: Subject to any disclaimer, the term of this patent is extended or adjusted under 35 U.S.C. 154(b) by 320 days.

(21) Appl. No.: 13/097,843

(22) Filed: Apr. 29, 2011

(65) Prior Publication Data

US 2012/0276616 A1    Nov. 1, 2012

(51) Int. Cl.
*B01D 53/02* (2006.01)
*B01D 50/00* (2006.01)

(52) U.S. Cl.
USPC ........ 95/92; 95/129; 95/135; 95/139; 95/141; 96/131; 96/134

(58) Field of Classification Search
USPC ............ 96/121, 122; 95/96, 143; 55/338, 340
See application file for complete search history.

(56) References Cited

U.S. PATENT DOCUMENTS

| | | | |
|---|---|---|---|
| 4,238,204 A | 12/1980 | Perry | |
| 4,398,926 A | 8/1983 | Doshi | |
| 4,645,516 A | 2/1987 | Doshi | |
| 4,654,063 A | 3/1987 | Auvil et al. | |
| 4,681,612 A | 7/1987 | O'Brien et al. | |
| 4,701,187 A | 10/1987 | Choe et al. | |
| 4,783,203 A | 11/1988 | Doshi | |
| 5,116,396 A | 5/1992 | Prasad et al. | |
| 5,207,806 A | 5/1993 | Lagree et al. | |
| 5,240,472 A | 8/1993 | Sircar | |
| 5,332,424 A | 7/1994 | Rao et al. | |
| 7,025,803 B2* | 4/2006 | Wascheck et al. | 95/50 |
| 7,575,624 B2 | 8/2009 | Cartwright et al. | |
| 7,731,779 B2 | 6/2010 | Palumbo | |
| 7,815,713 B2 | 10/2010 | Sorensen et al. | |

(Continued)

FOREIGN PATENT DOCUMENTS

| | | | | |
|---|---|---|---|---|
| EP | 0 804 272 B1 | 2/2002 | | |
| WO | WO 92/10270 | * | 6/1992 | ............. B01D 53/14 |
| WO | WO 2007/146281 A2 | 12/2007 | | |

OTHER PUBLICATIONS

Merichem—Lo-Cat™ Hydrogen Sulfide Removal System. Copyright Merichem Technologies. Aug. 28, 2010. Accessed May 7, 2013.*

*Primary Examiner* — Duane Smith
*Assistant Examiner* — Joubert X Glover
(74) *Attorney, Agent, or Firm* — Richard C Litman

(57) ABSTRACT

The method and system for methane separation and purification from a biogas includes collecting a raw Biogas gas stream having methane, carbon dioxide, water, sulfur compounds and non-methane organic compound (NMOC) constituents. The Biogas stream is fed into the intake of a liquid sulfur scrubber or a sulfur adsorber unit where the Biogas is separated into a main gas stream routed downstream in the system and a sulfur compounds stream removed from the system. The main gas stream is then processed by an NMOC absorber and further downstream, by an NMOC adsorber. NMOC produced by both NMOC processes is liquefied, removed from the system and stored. Upstream from the NMOC processes, the main gas stream is processed by at least one $CO_2$, $N_2$, $O_2$ gas separation unit that produces a usable product stream of enriched methane gas, and an off-gas stream, which a VPSAU processes for venting and recycling.

19 Claims, 1 Drawing Sheet

(56) References Cited

U.S. PATENT DOCUMENTS

| | | |
|---|---|---|
| 2006/0248921 A1 | 11/2006 | Hosford et al. |
| 2007/0095205 A1* | 5/2007 | Palumbo .......................... 95/51 |
| 2009/0216059 A1 | 8/2009 | Reyes et al. |
| 2010/0107872 A1 | 5/2010 | Bethell |
| 2010/0292524 A1 | 11/2010 | Turner et al. |
| 2011/0023710 A1 | 2/2011 | Sorensen et al. |

* cited by examiner

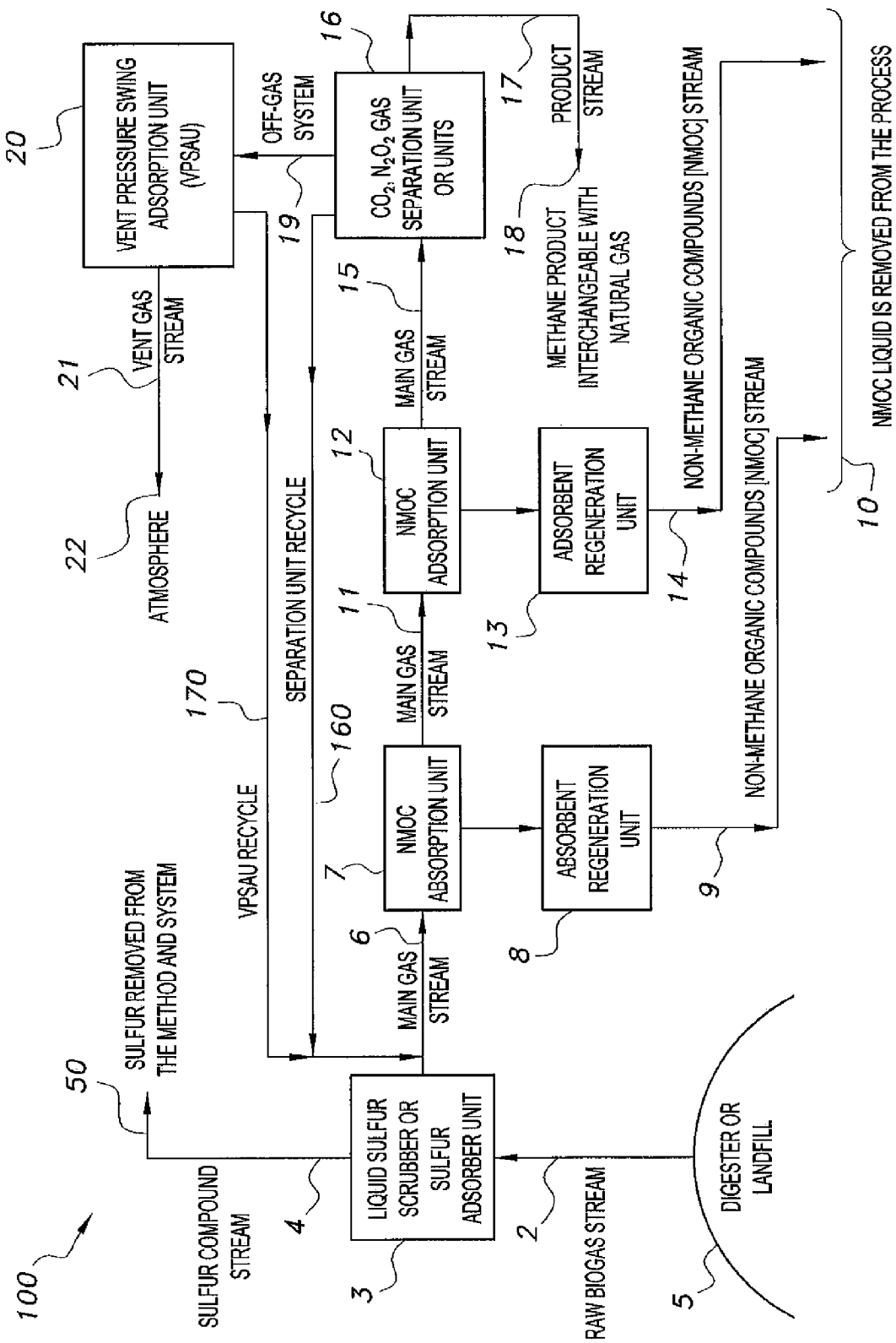

METHOD AND SYSTEM FOR METHANE SEPARATION AND PURIFICATION FROM A BIOGAS

BACKGROUND OF THE INVENTION

1. Field of the Invention

The present invention relates to the separation of gases and vapor compounds in a mixed stream, and particularly to a method and system for methane separation and purification from a biogas.

2. Description of the Related Art

Taking, separating and purifying methane from Biogas generating sources, such as anaerobic digesters and landfills, allows for use of the purified methane as a substitute for natural gas. A conventional process for isolating and recovering pure methane gas from Biogas requires that the collected non-methane organic compounds (NMOC) be thermally destroyed in engines, combustors, flares or thermoxidizers. This thermal destruction of the Biogas's non-methane organic compounds (NMOC) results in the creation of carbon dioxide (a greenhouse gas) that further adds to global warming.

The inventors know of no process capable of separating and purifying methane from Biogas gases without the creation of carbon dioxide from the inevitable thermal destruction phase of the Biogas's purification process. Therefore, there is a need for a method and system to separate Biogas gases, particularly non-methane organic compounds (NMOC), without the creation of carbon dioxide gas streams in order to provide a substantially purified methane stream interchangeable with natural gas.

Thus, a method and system for methane separation and purification from a biogas solving the aforementioned problems is desired.

SUMMARY OF THE INVENTION

The method and system for methane separation and purification from a biogas separates Biogas, purifies the usable methane, and collects the non-methane organic compounds (NMOC), thereby avoiding the thermal destruction of non-methane organic compounds and subsequent release of greenhouse gases to the atmosphere. The method collects a raw Biogas gas stream that includes methane, carbon dioxide, water, sulfur compounds and NMOC gases/vapors. The Biogas stream is fed into the intake of a liquid sulfur scrubber or a sulfur adsorber unit, where the Biogas is separated into a main gas stream routed downstream in the system and a sulfur compounds stream, which is removed from the system. The main gas stream is then processed by an NMOC absorber, and further downstream, by an NMOC adsorber. NMOC recovered by both NMOC processes is liquefied, removed from the system and stored.

Downstream from the NMOC processes, the main gas stream is processed by at least one $CO_2$, $N_2$, $O_2$ gas separation unit that produces a usable product stream of enriched methane gas, and an off-gas stream in which a vent pressure swing adsorption unit (VPSAU) processes the off-gas for venting and recycling.

These and other features of the present invention will become readily apparent upon further review of the following specification and drawings.

BRIEF DESCRIPTION OF THE DRAWINGS

The sole drawing FIGURE is a block diagram showing an exemplary system for methane separation and purification from Biogas according to the present invention.

Similar reference characters denote corresponding features consistently throughout the attached drawings.

DETAILED DESCRIPTION OF THE PREFERRED EMBODIMENTS

The method and system for methane separation and purification from a biogas separates the Biogas, purifies the usable methane, and collects the non-methane organic compounds (NMOC), thereby avoiding thermal destruction of the NMOC and resulting venting of greenhouse gases to the atmosphere. The method can collect a raw Biogas gas stream, which includes at least methane, carbon dioxide, water, sulfur compounds and NMOC gases/vapors. As shown in the drawing, the method separates the raw Biogas gas stream into at least one sulfur compounds stream and a main gas stream. It should be understood by persons of ordinary skill in the art that the flow of gas and liquid streams discussed herein may be facilitated by compressor and/or pump units disposed throughout the system 100. For each processing step of the system 100 described herein, such processing step may occur in a pressure vessel of suitable design to facilitate the described process. Moreover, required thermal and condensation operations may be facilitated by the use of heat exchangers throughout the system 100.

The anaerobic bacteria action on Waste in digesters or landfills 5 creates Biogas, which is fed into a conduit 2 to guide a raw Biogas stream, which comprises methane, carbon dioxide, water and non-methane organic compounds (NMOC) gas/vapors. Air may also find its way into the digesters/landfills 5 or raw Biogas gas stream 2 conduits, which adds additional gas separation requirements. Within the conduit system producing the Biogas stream 2, the raw Biogas stream 2 has a heating value of about 500 British thermal units (BTU) per cubic foot of gas, and the raw Biogas stream 2 also has the highest sulfur compound, carbon dioxide, oxygen, nitrogen, non-methane organic compounds (NMOC) at any point in the system.

The raw Biogas stream 2 is fed into a liquid sulfur scrubber or a sulfur adsorber unit 3, which oxidizes the inorganic sulfur compound hydrogen sulfide ($H_2S$) to elemental sulfur or sulfate, a safer and manageable compound.

The $H_2S$ separation unit 3 can be a gas-to-liquid sulfur scrubber that uses aerobic bacteria action to oxidize the inorganic sulfur compound hydrogen sulfide ($H_2S$) to elemental sulfur or sulfate. On the other hand, if the $H_2S$ separation unit 3 is an adsorber, a solid adsorption material is used to capture the $H_2S$. Both unit types convert $H_2S$ to safer and more manageable compounds, and this sulfur compound stream 4 is collected and removed at $H_2S$ removal point 50.

The Main Gas stream flows through the sulfur removal unit main gas effluent pipe 6, which feeds a NMOC absorption unit 7. The NMOC absorber is a gas-to-liquid scrubber that creates a first non-methane organic compounds (NMOC) stream 9 by using selective absorption of NMOC into a sponge solution disposed in the NMOC absorption unit 7. The gas-to-liquid scrubber NMOC absorption unit 7 absorbs NMOC in a continuous and or batch mode, which uses NMOC vapor pressure, temperature and selective absorption to absorb and collect NMOC as liquid in a pressure- and/or temperature-controlled sponge solution. The sponge solution containing the absorbed NMOC is regenerated by pressure and/or temperature, and the resulting NMOC liquid stream 9 is removed from the system and stored as a low grade fuel at a NMOC removal point 10.

The Main Gas stream continues its flow downstream through the system 100 via the NMOC absorption unit main gas effluent pipe 11, which feeds a NMOC adsorption unit 12. The NMOC adsorption unit 12 is a solid adsorbent bed that captures NMOC onto the surface and into the pores of the solid adsorption material. The NMOC are removed from the surface and pores of the adsorption material by regeneration of the adsorption material based on NMOC de-adsorption properties using temperature and or pressure to thereby create a second non-methane organic compounds (NMOC) stream 14, which is collected and removed from the system and stored as a low grade fuel at the NMOC removal point 10.

The Main Gas stream continues flowing downstream from the NMOC adsorption unit 12 via the NMOC adsorption unit main gas effluent pipe 15, which feeds at least one $CO_2$, $N_2$, $O_2$ gas separation unit 16. The resulting product gas stream 17 from the gas separation unit 16 is enriched in methane and depleted in carbon dioxide, oxygen, nitrogen, and NMOC relative to the main gas stream flowing through the NMOC adsorption unit effluent pipe 15 and entering the gas separation unit 16. The gas separation unit 16 may also produce a recycle stream 160 that is fed back downstream to an earlier separation step. An oxygen and nitrogen gas separation step may also be included in the gas separation unit 16 to produce a product gas stream 17 that is enriched in methane and depleted in carbon dioxide, oxygen, nitrogen, and NMOC. Preferably, the product gas stream 17 has a heating value of greater than 950 British thermal units (BTU) per cubic foot, and is of sufficient quality to allow the product gas 17 to be piped to a natural gas grid 18. The gas separation unit 16 also provides an off-gas stream 19 that is piped to a vent pressure swing adsorption unit (VPSAU) 20.

The off-gas gas stream 19 is depleted in methane and enriched in carbon dioxide, oxygen, and nitrogen with respect to the intake of the unit 16. The off-gas gas stream 19 may also contain a small amount of methane and NMOC. The Vent Pressure Swing Adsorption Unit (VPSAU) 20 collects the small amount of methane and NMOC that are in the off-gas stream 19 and forms a VPSAU recycle stream 170 that is sent back and mixed with the main gas stream at an earlier step of the method. The VPSAU recycle stream 170 is depleted in carbon dioxide, oxygen, nitrogen, but is enriched in methane and NMOC relative to the off-gas stream 19. The VPSAU 20 also produces a vent gas stream 21, which is depleted in methane and NMOC, but is enriched in anaerobic generated carbon dioxide, oxygen, and nitrogen that is vented into the atmosphere 22. A test of the vent gas stream 21 gas quality shows that there was a greater than 98 weight-percent emission reduction of total non-methane organic compounds (NMOC) relative to the raw Biogas gas input stream at the intake conduit 2.

EXAMPLE

This example shows work completed at the Waste Management South Hills landfill site in South Park, Pa. This example demonstrates that a raw Biogas gas stream processed by the system 100 can be successfully functionally tested and documented. The test used an Ametek ProLine Mass Spectrometer as the primary test instrument to confirm gas quality and test results. Waste Management's landfill with raw Biogas, ARC Technologies Corporation's existing gas purification system comprised of an $H_2S$ scrubber, a non-methane organic compounds (NMOC) absorption unit that collects and liquefies the NMOC, a non-methane organic compounds (NMOC) adsorption bed unit that collects and liquefies the NMOC, a newly added test Vent Pressure Swing Adsorption Unit (VPSAU) that collects/returns methane and NMOC back to the inlet of the Gas purification system, and compression and all associated piping/controls. The Vent Pressure Swing Adsorption Unit (VPSAU) also allows for the venting of the anaerobically generated carbon dioxide and air from the biogas gas purification method and system.

According to the tests, a raw Biogas gas stream was recovered from a Biogas source (landfill) via a gas collection system. The Raw Biogas gas stream was approximately 54 mole percent methane, 38 mole percent carbon dioxide, 4 mole percent nitrogen, 0.4 mole percent oxygen, about 4000 ppmv of non-methane organic compounds (NMOC), 60 ppm of sulfur compounds, and was saturated with water vapor. The flow rate of the raw Biogas gas stream is approximately 800,000 cubic feet per day. The test used the Mass Spectrometer mass numbers 72 to 92, and 84 peak points within these mass numbers to summarize the peak current value that gave a total raw gas NMOC instance of $5.446488545E^{-11}$ amps.

After the raw Biogas gas stream was processed by the system 100, the NMOC liquid stream was collected, removed from the site, and was approved by the State of Pennsylvania to be used as a low grade heating fuel. The exiting gas from the NMOC scrubber has a reduction in NMOC proven by a quantity of 3.8 gallons of liquids removed from the absorption unit in a 24-hour period.

The exiting gas from the NMOC scrubber had a reduction in NMOC proven by a quantity of 55 gallons of liquid removed from the one regenerated cycle of the NMOC adsorption bed that was active for a 20-day period.

The Vent gas at the VPSAU 20 was tested using the Mass Spectrometer mass numbers 72 to 92 and the same 84 peak points within these mass numbers to summarize the peak current value that gave a total vent gas NMOC instance of $9.16398E^{-13}$ amps. This $9.16398E^{-13}$ (vent gas NMOC)/$5.446488545E^{-11}$ (raw gas NMOC)$=1.68E^{-02}$ or 1.68% of the raw gas NMOC amps, which was a 98.3% reduction of total non-methane organic compounds (NMOC) relative to the raw Biogas gas stream at the intake conduit 2. The system 100 is formed from commercially available individual components, which, when combined as described above, will convert landfill gas to a usable natural gas, which can be fed into a natural gas grid. The system may be erected at a landfill, waste gas site, or the like.

It is to be understood that the present invention is not limited to the embodiments described above, but encompasses any and all embodiments within the scope of the following claims.

We claim:
1. A method for methane separation and purification from a biogas, comprising the steps of:
  collecting a raw Biogas stream, the raw Biogas stream including at least methane, carbon dioxide,
water, hydrogen sulfide, and non-methane organic compounds (NMOC);
  performing a raw Biogas stream separation procedure in which the raw Biogas stream is separated into a sulfur compounds stream and a main gas stream, the sulfur compounds stream being removed from further processing, the main gas stream being purified from the hydrogen sulfide;
  adsorbing a non-methane organic compounds (NMOC) liquid stream from the main gas stream, the NMOC liquid stream being removed from further processing, the main gas stream being substantially purified from the non-methane organic compounds;
  performing a main gas stream separation procedure in which the main gas stream is separated into an off-gas stream substantially composed of carbon dioxide, nitro- gen, and oxygen gas, and a product stream composed substantially of purified methane gas;

performing an off-gas stream adsorbing procedure, thereby forming a vent gas stream and a recycle stream;

venting the vent gas stream into the atmosphere without flaring the vent gas stream; and mixing the recycle stream with the main gas stream after the step of performing a raw Biogas stream separation procedure and before the step of absorbing a first non-methane organic compounds (NMOC) liquid stream.

2. The method for methane separation and purification from a biogas according to claim 1, wherein said step of performing a main gas stream separation procedure further comprises the steps of producing a recycle stream and feeding the recycle stream into the main gas stream after the step of performing a raw Biogas stream separation procedure and before the step of absorbing a first non-methane organic compounds (NMOC) liquid stream.

3. The method for methane separation and purification from a biogas according to claim 1, further comprising the step of absorbing a second non-methane organic compounds (NMOC) liquid stream from the main gas stream prior to said step of performing a main gas stream separation procedure, the second NMOC liquid stream being removed from further processing, the main gas stream being partially purified by removal of the absorbed non-methane organic compounds.

4. The method for methane separation and purification from a biogas according to claim 3, wherein said NMOC absorbing step further comprises the steps of:
utilizing a sponge solution to absorb the NMOC; and
thermodynamically regenerating the sponge solution as a function of a vapor point pressure of the NMOC stream and the sponge solution.

5. The method for methane separation and purification from a biogas according to claim 1, wherein said step of performing an off-gas stream adsorbing procedure further comprises the step of forcing said off-gas stream to come in contact with nanoporous and or microporous adsorbent materials selective for methane and non-methane organic compounds (NMOC) and nonselective for carbon dioxide, oxygen, and nitrogen.

6. The method for methane separation and purification from a biogas according to claim 1, wherein said raw Biogas stream separation procedure further comprises the step of using a solid adsorption material to capture the hydrogen sulfide (H2S) for removal from the raw Biogas stream.

7. The method for methane separation and purification from a biogas according to claim 1, wherein said raw Biogas stream separation procedure further comprises the step of using aerobic bacteria action to oxidize inorganic sulfur compounds, including hydrogen sulfide (H2S), to elemental sulfur or sulfates for removal from the raw Biogas stream.

8. The method for methane separation and purification from a biogas according to claim 1, wherein said step of adsorbing a non-methane organic compounds (NMOC) liquid stream further comprises the step of using adhesion of molecules of the NMOCs to surfaces and pores of selective adsorbent materials.

9. The method for methane separation and purification from a biogas according to claim 8, further comprising the step of regenerating said selective adsorbent materials by exposing said selective adsorbent materials to a carrier gas with temperature and pressure control in order to reverse adhesion of the NMOC molecules to said selective adsorbent materials, thereby creating a mixed NMOC gas carrier stream.

10. The method for methane separation and purification from a biogas according to claim 9, further comprising the step of condensing the NMOC out of the mixed NMOC gas carrier stream in order to form a NMOC liquid stream.

11. A system for methane separation and purification from a biogas stream, comprising:
means for collecting a raw Biogas stream, the raw Biogas stream including methane, carbon dioxide, water, hydrogen sulfide, and non-methane organic compounds (NMOC);
means for processing the raw biogas stream to send a portion thereof downstream as a main gas stream for further processing;
means for separating the non-methane organic compounds (NMOC) from the main gas stream;
at least one CO2, N2, O2 gas separation unit accepting the main gas stream downstream from the means for separating the non-methane organic compounds, the at least one CO2, N2, O2 gas separation unit producing a methane-enriched product stream and a CO2, N2, O2 gas-enriched off gas stream;
a vent pressure swing adsorption unit (VPSAU) accepting the CO2, N2, O2 gas-enriched off gas stream, the VPSAU producing a vent gas stream and a VPSAU recycle stream;
means for venting the vent gas stream into the atmosphere without flaring the vent gas stream; and
means for recycling the VPSAU recycle stream upstream of the VPSAU.

12. The system for methane separation and purification according to claim 11, further comprising a liquid sulfur scrubber disposed between said raw biogas stream and said main gas stream.

13. The system for methane separation and purification according to claim 11, further comprising an aerobic bacteria sulfur oxidizer disposed between the raw biogas stream and the main gas stream.

14. The system for methane separation and purification according to claim 11, wherein said means for separating said non-methane organic compounds (NMOC) from said main gas stream further comprises:
means for utilizing a sponge solution to absorb the NMOC; and
means for thermodynamically regenerating said sponge solution as a function of a vapor point pressure of the NMOC stream and the sponge solution.

15. The system for methane separation and purification according to claim 11, wherein said vent pressure swing adsorption unit (VPSAU) further comprises adsorbent materials selective for methane and non-methane organic compounds (NMOC) and nonselective for carbon dioxide, oxygen, and nitrogen.

16. The system for methane separation and purification according to claim 11, wherein said means for separating the non-methane organic compounds (NMOC) from the main gas stream further comprises means for adsorbing the NMOC using adhesion of molecules of the NMOC to surfaces and pores of selective adsorbent materials.

17. The system for methane separation and purification according to claim 16, wherein said means for adsorbing the NMOC further comprises means for regenerating said selective adsorbent materials by exposing said selective adsorbent materials to a carrier gas with temperature and pressure control, thereby reversing adhesion of the NMOC in order to form a mixed NMOC gas carrier stream.

18. The system for methane separation and purification according to claim 17, wherein said means for adsorbing the NMOC further comprises means for condensing the NMOC out of the mixed NMOC gas carrier stream.

19. The system for methane separation and purification according to claim 11, wherein said at least one CO2, N2, O2 gas separation unit further comprises means for producing a recycle stream and for feeding the recycle stream back upstream of said at least one CO2, N2, O2 gas separation unit.

* * * * *